(12) United States Patent
Asplin et al.

(10) Patent No.: US 6,991,937 B2
(45) Date of Patent: Jan. 31, 2006

(54) URINE CYSTINE QUANTITATION AND SUPERSATURATION ASSAY

(75) Inventors: John R. Asplin, Chicago, IL (US); Fredric L. Coe, Chicago, IL (US)

(73) Assignee: Litholink Corporation, Chicago, IL (US)

( * ) Notice: Subject to any disclaimer, the term of this patent is extended or adjusted under 35 U.S.C. 154(b) by 500 days.

(21) Appl. No.: 10/062,276

(22) Filed: Oct. 26, 2001

(65) Prior Publication Data

US 2003/0087449 A1 May 8, 2003

(51) Int. Cl.
*G01N 33/68* (2006.01)
(52) U.S. Cl. .............................. 436/89; 436/86; 436/63; 436/100
(58) Field of Classification Search ................. 436/86, 436/89, 174, 183, 63, 100; 422/61; 435/810
See application file for complete search history.

(56) References Cited

U.S. PATENT DOCUMENTS 6,413,778 B1 * 7/2002 Carpenter et al. ............. 436/4

OTHER PUBLICATIONS

Coe et al. The Journal of Urology, vol. 166, Aug. 2001, pp. 688-693.*
Goldfarb et al. Cystine Supersaturation (CSS) Measurements in Patients Taking Cystine-Binding Thiol Drugs (CBTD). Journal of the American Society of Nephrology, 12 (Program and Abstract Issue), p. 552A, Sep. 2001.*
Chow, G.K. and Streem, S.B. 1996. "Medical treatment of cystinuria: results of contemporary clinical practice," *J Urol* 156:1576-1578.
Dent, C.E. and Senior, B. 1955. "Studies on the treatment of cystinuria," *Br J Urol* 27:317-332.
Kaniowska, et al. 1998. "Urinary excretion measurement of cysteine and homocysteine in the form of their S-pyridinium derivatives by high-performance liquid chromatography with ultraviolet detection," *J Chromatog* 798:27-35.
Kelly S. 1978. "Cystinuria genotypes predicted from excretion patterns," *Am J Med Genet* 2:175-190.
Kuhara, et al., 1999. "Pilot study of gas chromatographic-mass spectrometric screening of newborn urine for inborn errors of metabolism after treatment with urease," *J Chromatog B* 731:141-147.
Lotz, M. and Potts, J.T. 1965. "Rapid, simple method for determining effectiveness of d-penicillamine therapy in cystinuria," *Br Med J* 2:521.
Marshall, R.W. and Robertson, W.G. 1976. "Nomograms for the estimation of the saturation of urine with calcium oxalate, calcium phosphate, magnesium ammonium phosphate, uric acid, sodium acid urate, ammonium acid urate, and cystine," *Clin Chim Acta* 72:253-260.
Nakagawa, Y. and Coe, F.L. 1999. "A modified cyanide-nitroprusside method for quantifying urinary cystine concentration that corrects for creatinine interference," *Clin Chim Acta* 28:57-68.
Nakagawa, et al. 2000. "Clinical use of cystine supersaturation measurements," *J Urol* 164:1481-1485.
Pak, C.Y.C. and Fuller, C.J. 1983. "Assessment of cystine solubility in urine and of heterogenous nucleation," *J Urol* 129:1066-1070.
Pak, et al.1986. "Management of cystine nephrolithiasis with alpha-mercaptopropionaoglycine," *J Urol* 136:1003-1008.
Pastore, et al. 1998. "Fully automated assay for total homocysteine, cysteine, cysteinylglycine, glutathione, cysteamine, and 2 mercaptopropionylglycine in plasma and urine," *Clin Chem* 44:825-832.
Roesel, R.A. and Coryell, M.E. 1974. "Determination of cystine excretion by the nitroprusside method during drug therapy of cystinuria," *Clin Chim Acta* 52:343-346.

* cited by examiner

*Primary Examiner*—Maureen M. Wallenhorst
(74) *Attorney, Agent, or Firm*—Sidley Austin Brown & Wood (57) ABSTRACT

A method for measuring cystine supersaturation of a patient urine sample as an indicator of the patient's risk for cystine stone formation has been found. A method for collecting a patient urine sample for assessment of cystine concentration and cystine supersaturation has also been found.

17 Claims, 5 Drawing Sheets

URINE CYSTINE QUANTITATION AND SUPERSATURATION ASSAY

TECHNICAL FIELD OF INVENTION

This invention relates to a chemical assay of a body fluid.

BACKGROUND

Cystinuria is an inherited defect of the renal tubules in which resorption of the amino acid cystine is impaired, urinary excretion is increased, and cystine calculi often form in the urinary tract. The diminished renal tubular resorption of cystine leads to an increase in cystine concentration in the urine. Since cystine is poorly soluble in acidic or neutral urine, the concentration of cystine in the urine can exceed its solubility, leading to supersaturation of urine with cystine and resulting in precipitation as cystine crystals or stones. Recurring cystine calculi can lead to urinary infection, obstruction, and possible loss of renal function. Treatment methods are aimed at reducing cystine excretion and increasing the solubility of cystine by means of (1) dietary restriction to limit cystine production and excretion, e.g., limiting the intake of sulfur-containing amino acids and reducing dietary sodium, (2) use of physical means to increase cystine solubility such as enhanced fluid intake or alkalinization of urine above pH 7.5, and (3) administration of drugs which contain thiol groups such as D-penicillamine, tiopronin, or captopril which bind cystine and convert it to a more soluble compound. Yet, despite the various treatment methods available, clinical reports indicate that formation of cystine stones continues to be a problem for cystinuric patients (Chow, G. K. and Streem, S. B. 1996. "Medical treatment of cystinuria: results of contemporary clinical practice," *J Urol* 156:1576–1578; Pak, et al. 1986. "Management of cystine nephrolithiasis with alpha-mercaptopropionaoglycine," *J Urol* 136:1003–1008).

Several qualitative and quantitative tests have been used to diagnose and treat cystinuria. One such test is a calorimetric method using sodium cyanide and sodium nitroprusside (Nakagawa, Y. and Coe, F. L. 1999. "A modified cyanide-nitroprusside method for quantifying urinary cystine concentration that corrects for creatinine interference," *Clin Chim Acta* 28:57–68). Other preferred quantitative methods involves precolumn derivatization followed by reversed-phase high performance liquid chromatography (HPLC) or gas chromatography (Kaniowska, et al. 1998. "Urinary excretion measurement of cysteine and homocysteine in the form of their S-pyridinium derivatives by high-performance liquid chromatography with ultraviolet detection," *J Chromatog* 798:27–35; Pastore, et al. 1998. "Fully automated assay for total homocysteine, cysteine, cysteinylglycine, glutathione, cysteamine, and 2 mercaptopropionylglycine in plasma and urine," *Clin Chem* 44:825–832; and Kuhara, et al. 1999. "Pilot study of gas chromatographic-mass spectrometric screening of newborn urine for inborn errors of metabolism after treatment with urease," *J Chromatog B* 731:141–147). Despite the available methods for determining urine cystine concentration, it has been reported that urine cystine concentration alone was not an adequate predictor for cystine supersaturation (Nakagawa, et al. 2000. "Clinical use of cystine supersaturation measurements," *J Urol* 164:1481–1485; and Pak, C. Y. C. and Fuller, C. J. 1983. "Assessment of cystine solubility in urine and of heterogeneous nucleation," *J Urol* 129:1066–1070).

Clinical evaluation and treatment for cystine stone formation in a given cystinuric patient should be monitored by the assessment of urine cystine supersaturation. When cystine concentration in the urine exceeds cystine solubility, the urine is said to be supersaturated with cystine, which can lead to crystallization of cystine and stone formation. To determine the cystine supersaturation point of a urine specimen, one must know not only the cystine concentration but also the solubility of cystine in the urine. Nomograms relating cystine solubility to pH have been widely used in estimating urine cystine saturation (See Dent, C. E. and Senior, B. 1955. "Studies on the treatment of cystinuria," *Br J Urol* 27:317–332; and Marshall, R. W. and Robertson, W. G. 1976. "Nomograms for the estimation of the saturation of urine with calcium oxalate, calcium phosphate, magnesium ammonium phosphate, uric acid, sodium acid urate, ammonium acid urate, and cystine," *Clin Chim Acta* 72:253–260). Pak and Fuller and Nagakawa et al reported that (1) factors such as electrolyte and macromolecule concentration in a given urine sample can affect cystine solubility, (2) the electrolyte and macromolecular content is variable, (3) the saturation of urine with respect to cystine can not be accurately estimated by comparing a measured urinary cystine concentration to a cystine solubility curve such as that proposed by Dent and Senior, and (4) cystine saturation must be derived from the direct measurement of cystine solubility of a patient's urine sample. An empirical method was proposed wherein the original cystine concentration in a patient sample was measured, solid cystine added to an aliquot of the urine and incubated for 2 days at 37° C. keeping a constant pH, remaining solid cystine filtered from the urine sample, cystine concentration in the filtrate measured, and the original cystine concentration divided by the cystine concentration in the filtrate to give a cystine concentration ratio, wherein a value of 1 represented saturation, a value of greater than 1 represented supersaturation, and a value of less than 1 represented undersaturation. In this assay, undersaturation was indicated by dissolution of the added cystine in the urine; and supersaturation was indicated by an increase in solid cystine (Pak, C. Y. C. and Fuller, C. J. 1983. *J Urol* 129:1066–1070; and Nakagawa, et al. 2000. *J Urol* 164:1481–1485).

While the empirical method described in these two papers provides an accurate measurement of urine cystine supersaturation, there is no consideration given to many of the factors which may affect the assay results. Crystallization of cystine during the collection of a 24-hour urine may lead to underestimation of cystine concentration and supersaturation (Kelly S. 1978. "Cystinuria genotypes predicted from excretion patterns," *Am J Med Genet* 2:175–190). In addition, use of thiol-containing drugs such as D-penicillamine, tiopronin, and captopril complicate the measurement of urine cystine concentration and supersaturation (Lotz, M. and Potts, J. T. 1965. "Rapid, simple method for determining effectiveness of d-penicillamine therapy in cystinuria," *Br Med J* 2:521; and Roesel, R. A. and Coryell, M. E. 1974. "Determination of cystine excretion by the nitroprusside method during drug therapy of cystinuria," *Clin Chim Acta* 52:343–346). Colorimetric assays relying on a reduction reaction are greatly affected by these drugs. Even in HPLC and amino acid chromatography, techniques which are reported to allow assaying of both drug-bound and unbound cystine in treated patient, the conditions of these assay methods may alter cystine-drug binding so that the true amount of unbound cystine cannot be accurately determined. Thus, there is a need for methods to accurately measure urine cystine concentration and cystine supersaturation wherein the methods are not affected by collection and assay conditions. Further, the drugs used to treat cystinuria have a high incidence of serious adverse side effects, making it advantageous to prescribe the minimum effective dose for a given patient. Therefore, there is a need for methods that provide an accurate index of supersaturation while the drugs are in use.

A novel collection method and solid phase assay have now been found that provides an accurate measurement of urine cystine supersaturation, even when the patient is being treated with therapeutic cystine-binding drugs. The assay provides a means by which clinically reliable measures of overall treatment success in lowering the degree of urine cystine supersaturation and, therefore, risk of stone formation can be accurately assessed.

SUMMARY OF THE INVENTION

In one aspect, the invention is a method for determining the level of cystine supersaturation in a patient urine sample comprising adding to a patient urine sample a measured amount of solid phase cystine to form a cystine/urine sample; incubating the cystine/urine sample under conditions that permit dissolution of the solid phase cystine until equilibrium is reached with undissolved residual solid phase cystine to form an equilibrium mixture; separating the residual solid phase cystine from the equilibrium mixture to form a cystine pellet; completely dissolving the cystine pellet in a cystine-dissolving agent to form a final cystine solution; measuring the amount of cystine dissolved in the final cystine solution; and subtracting the amount of cystine dissolved in the final cystine solution from the measured amount of solid phase cystine to obtain a calculated value for the amount of dissolved solid phase cystine in the equilibrium mixture, whereby the amount of dissolved solid phase cystine in the equilibrium mixture is an indicator of urine cystine supersaturation. In one embodiment, the patient urine sample is an aliquot of voided urine collected over a 24-hour period. In a preferred embodiment, the final cystine solution has a pH greater than pH 9 and the cystine-dissolving agent is selected from the group consisting of sodium carbonate, sodium bicarbonate, lithium carbonate, sodium hydroxide and potassium hydroxide. In another preferred embodiment, the final cystine solution has a pH less than pH 2, and the cystine-dissolving agent is selected from the group consisting of hydrochloric acid, sulfuric acid, phosphoric acid, and nitric acid.

In another aspect, the invention is a method for measuring a patient's risk for cystine stone formation comprising adding to a first patient urine sample at a first time point a measured first amount of solid phase cystine to form a first cystine/urine sample; incubating the first cystine/urine sample under conditions that permit dissolution of the solid phase cystine until equilibrium is reached with undissolved residual solid phase cystine to form a first equilibrium mixture; separating the first residual solid phase cystine from the first equilibrium mixture to form a first cystine pellet; completely dissolving the first cystine pellet in a first cystine-dissolving agent to form a first final cystine solution; measuring the amount of cystine dissolved in the first final cystine solution; subtracting the amount of cystine dissolved in the first final cystine solution from the first measured amount of solid phase cystine to obtain a calculated value for the amount of dissolved solid phase cystine in the first equilibrium mixture; at a second time point adding to a second patient urine sample collected under the same conditions as the first patient urine sample a measured second amount of solid phase cystine to form a second cystine/urine sample; incubating the second cystine/urine sample under conditions that permit dissolution of the solid phase cystine until equilibrium is reached with undissolved residual solid phase cystine to form a second equilibrium mixture; separating the second residual solid phase cystine from the second equilibrium mixture to form a second cystine pellet; completely dissolving the second cystine pellet in a second cystine-dissolving agent, the first cystine-dissolving agent and the second cystine-dissolving agent being the same or different, to form a second final cystine solution; measuring the amount of cystine dissolved in the second final cystine solution; subtracting the amount of cystine dissolved in the second final cystine solution from the second measured amount of solid phase cystine to obtain a calculated value for the amount of dissolved solid phase cystine in the second equilibrium mixture; and comparing the amount of dissolved solid phase cystine in the first equilibrium mixture to the amount of dissolved solid phase cystine in the second equilibrium mixture, whereby an increase in the amount of dissolved solid phase cystine in the second equilibrium mixture over the amount of dissolved solid phase cystine in the first equilibrium mixture is equated with a lesser risk of cystine stone formation in the patient and a decrease in the amount of dissolved solid phase cystine in the second equilibrium mixture over the amount of dissolved solid phase cystine in the first equilibrium mixture is equated with a greater risk of cystine stone formation in the patient. In one embodiment, the first patient urine sample is an aliquot of a urine collection voided over a 24-hour period at the first time point and the second patient urine sample is an aliquot of a urine collection voided over a 24-hour period at the second time point. Preferably, the pH of the first final cystine solution is greater than pH 9 or less than pH 2 and the pH of the second final cystine solution is greater than pH 9 or less than pH 2. A preferred cystine-dissolving agent is selected from the group consisting of sodium carbonate, sodium bicarbonate, lithium carbonate, sodium hydroxide potassium hydroxide, hydrochloric acid, sulfuric acid, phosphoric acid, and nitric acid.

In another aspect, the invention is a method for collecting patient urine useful for measuring cystine concentration and cystine supersaturation comprising collecting voided urine over time in a collection receptacle to form an untreated urine collection; transferring an aliquot of the untreated urine collection to a second container to form an untreated urine sample; adding to the remainder of the untreated urine collection an effective amount of a cystine-dissolving agent to completely dissolve any crystallized cystine present in the urine collection to form a treated urine collection having a pH greater than pH 9 or less than pH 2, whereby the untreated urine sample is useful for measuring cystine concentration and cystine supersaturation and the treated urine collection is useful for measuring cystine concentration. In one embodiment, the patient collects voided urine over a 24-hour period to form the untreated urine collection. A preferred cystine-dissolving agent is selected from the group consisting of sodium carbonate, sodium bicarbonate, lithium carbonate, sodium hydroxide, potassium hydroxide, hydrochloric acid, sulfuric acid, phosphoric acid, and nitric acid.

In another aspect, the invention is a method for determining cystine concentration in a patient urine comprising collecting voided urine over time in a collection receptacle to form an untreated urine collection; transferring an aliquot of the untreated urine collection to a second container to form an untreated urine sample; adding to the untreated urine collection an effective amount of a cystine-dissolving agent to completely dissolve any crystallized cystine present in the urine collection to form a treated urine collection having a pH greater than pH 9 or less than pH 2; measuring the cystine concentration in the treated urine collection and in the untreated urine sample; comparing the cystine concentration in the treated urine collection to the cystine concentration in the untreated urine sample, concluding that the cystine concentration of the patient urine is the measured cystine concentration of the untreated urine sample if the measured cystine concentration of the treated urine collection is less than or equal to the measured cystine concentration of the untreated urine collection or concluding that the cystine concentration of the patient urine is the measured cystine concentration of the treated urine collection if the measured cystine concentration of the treated urine collection is higher than the measured cystine concentration of the untreated urine sample. In one embodiment, the patient collects voided urine over a 24-hour period to form the untreated urine collection. A preferred cystine-dissolving agent is selected from the group consisting of sodium carbonate, sodium bicarbonate, lithium carbonate, sodium hydroxide, potassium hydroxide, hydrochloric acid, sulfuric acid, phosphoric acid, and nitric acid.

In yet another aspect, the invention is a method for determining cystine concentration and the amount of cystine supersaturation in a patient urine sample comprising collecting voided urine over time in a collection receptacle to form an untreated urine collection; transferring an aliquot of the untreated urine collection to a second container to form an untreated urine sample; adding to the untreated urine collection an effective amount of a cystine-dissolving agent to completely dissolve any crystallized cystine present in the urine collection to form a treated urine collection; determining the cystine concentration in the treated urine collection and the untreated urine sample; comparing the cystine concentration in the treated urine collection to the cystine concentration in the untreated urine sample; adding to an aliquot of the untreated urine sample a measured amount of solid phase cystine to form a cystine/urine sample; incubating the cystine/urine sample under conditions that permit dissolution of the solid phase cystine until equilibrium is reached with undissolved residual solid phase cystine to form an equilibrium mixture; separating the residual solid phase cystine from the equilibrium mixture to form a cystine pellet; completely dissolving the cystine pellet in a cystine-dissolving agent to form a final cystine solution; measuring the amount of cystine dissolved in the final cystine solution; and subtracting the amount of cystine dissolved in the final cystine solution from the measured amount of solid phase cystine to obtain a calculated value for the amount of dissolved solid phase cystine in the equilibrium mixture, whereby the amount of dissolved solid phase cystine is an indicator of urine cystine supersaturation and concluding that the cystine concentration of the patient urine is the measured cystine concentration of the untreated urine sample if the measured cystine concentration of the treated urine collection is less than or equal to the measured cystine concentration of the untreated urine collection or concluding that the cystine concentration of the patient urine is the measured cystine concentration of the treated urine collection if the measured cystine concentration of the treated urine collection is higher than the measured cystine concentration of the untreated urine sample. In one embodiment, the patient collects voided urine over a 24-hour period to form said untreated urine collection. Preferably, the pH of the treated urine collection is greater than pH 9 or less than pH 2 and the pH of the final cystine solution is greater than pH 9 or less than pH 2. A preferred cystine-dissolving agent is selected from the group consisting of sodium carbonate, sodium bicarbonate, lithium carbonate, sodium hydroxide, potassium hydroxide, hydrochloric acid, sulfuric acid, phosphoric acid, and nitric acid.

In yet another aspect, the invention is a urine collection kit specific for obtaining urine samples suitable for the measurement of cystine concentration and cystine supersaturation comprising a urine collection receptacle of suitable size to collect a volume of untreated urine; a quantity of cystine-dissolving agent suitable for alkalinizing or acidifying the volume of untreated collected urine; and instructions describing the method for collecting urine and dispensing of the cystine-dissolving agent into the untreated collected urine to form a treated urine. In one embodiment, the kit further comprises transport containers suitable for transporting an aliquot of untreated collected urine and an aliquot of the treated urine.

In yet another aspect, the invention is a urine collection kit specific for obtaining urine samples suitable for the measurement of cystine concentration and cystine supersaturation comprising a urine collection receptacle of suitable size to collect a volume of untreated urine and comprising a quantity of cystine-dissolving agent suitable for alkalinizing or acidifying the volume of untreated collected urine to form a treated urine; and instructions describing the method for collecting urine to form a treated urine. In one embodiment, the kit further comprises transport containers suitable for transporting an aliquot of untreated collected urine and an aliquot of the treated urine.

DESCRIPTION OF DRAWINGS

FIGS. 2A and 2B depict the dissolution of solid phase cystine by D-penicillamine. The dashed horizontal line depicts the maximum cystine concentration that could be attained if all available solid phase cystine went into solution. Added to buffer (FIG. 2A; circles) or normal urine (FIG. 2B; circles), D-penicillamine dissolved cystine progressively with a molar proportion of 0.24±0.01 and 0.21±0.008 mole/mole in buffer and urine, respectively. Direct solution measurements (triangles) gave artificially low values with little slope dependence.

FIGS. 3A and 3B depict the dissolution of solid phase cystine by tiopronin. The dashed horizontal line depicts the maximum cystine concentration that could be attained if all available solid phase cystine went into solution. Added to buffer (FIG. 3A; circles) or normal urine (FIG. 3B; circles), tiopronin dissolved cystine progressively with a molar proportion of 0.41±0.02 and 0.36±0.01 mole/mole in buffer and urine, respectively. Direct solution measurements (triangles) gave reasonably close correspondence with solid phase measurements.

FIGS. 4A and 4B depict dissolution of solid phase cystine by captopril. The dashed horizontal line depicts the maximum cystine concentration that could be attained if all available solid phase cystine went into solution. Added to buffer (FIG. 4A; circles) or normal urine (FIG. 4B; circles), captopril dissolved cystine progressively with a molar proportion of 0.36±0.04 and 0.35±0.01 mole/mole in buffer and urine, respectively. Direct solution measurements (triangles) gave progressive rise of apparent cystine concentration, far above the amount available in the solid phase.

FIGS. 5A and 5B depict the effect of thiol drugs on a reducing assay for cystine. When added to a buffer solution, cystine (FIG. 5A; triangles) and captopril (circles) show the same intensity signal (absorbance, y-axis) with a reducing assay at equivalent molarities. Tiopronin (pentagons) and d-penicillamine (squares) have less activity than cystine in the reducing assay and require much greater concentrations to achieve similar levels of intensity. When added to a buffer saturated with cystine (FIG. 5B), the drugs all increase the absorbance of the reducing reaction (apparent cystine concentration, y-axis), with captopril (circles) having the greatest effect. The symbols are defined as in FIG. 5A.

DETAILED DESCRIPTION

An assay to detect cystinuria, to quantitate cystine excretion, to assess the propensity of a patient to develop cystine stones, or to determine the effectiveness of ongoing treatments for cystinuria has been developed. In general, extraneous solid phase cystine is added to a test sample under conditions appropriate for supersaturation to occur and the amount of extraneous solid phase cystine required to reach supersaturation is measured. A method of urine collection suitable for measuring cystine supersaturation and cystine concentration of the collected urine has also been found.

As used herein, any solid phase cystine may be used including both L- and D-cystine or a mixture of the two. For example, L-cystine (Sigma Aldrich Corp, St Louis, Mo., Catalog # C-6195) may be used as solid phase cystine.

Cystine solubility increases at extremes of pH, either very high or very low. As used herein, a cystine-dissolving agent is any substance which can raise the pH of a urine collection, or any cystine-containing sample, to above pH 9 or below pH 2 without affecting the cystine concentration or its measurement. For example, to bring a patient's 24-hour urine collection to below pH 2, at least 200 meq of an inorganic acid is preferably used. To bring a patient's 24-hour urine collection to greater than pH 9, at least 125 mmoles of a buffer with a pH between pH 9.5 and pH 11 or at least 100 meq of a strong alkali solution is preferably used. Exemplary cystine-dissolving agents for raising the pH to above pH 9 include but are not limited to sodium carbonate, sodium bicarbonate, lithium carbonate, sodium hydroxide, and potassium hydroxide. Exemplary cystine-dissolving agents for lowering the pH to below pH 2 include but are not limited to hydrochloric acid, sulfuric acid, phosphoric acid, and nitric acid. A preferred cystine-dissolving agent is sodium carbonate useful in dissolving cystine in a 24-hour urine collection at an effective amount of 15 grams. A preferred cystine-dissolving agent useful in completely dissolving the residual solid phase cystine remaining at the end of the assay of the present invention is 0.1 M sodium carbonate, pH 9.9 (Sigma Aldrich Corp, Catalog # S-7795). It is to be understood that the cystine-dissolving agent used in various steps of the urine collection method and cystine supersaturation assay of the present invention can be the same or different.

As used herein, an incubation buffer has similar sodium, chloride, and phosphate concentrations as can be found in normal human urine. A preferred incubation buffer system is phosphate buffered saline and most preferably, 0.01 M phosphate, 0.0027 M potassium chloride, 0.137 M sodium chloride, pH 7.4 (Sigma Aldrich Corp, Catalog # P-4417).

The assay of the present invention provides for measurement of urine cystine supersaturation even when the patient from which the urine sample is collected is undergoing treatment with therapeutic cystine-binding drugs. The assay provides for direct measurement of supersaturation, and because supersaturation is the relevant driving force for crystallization in cystinuria, the resulting data can be used to assess the propensity of a patient to develop cystine stones as well as to determine the effectiveness of ongoing treatments.

Because the excretion and urinary concentration of cystine varies with the patient's activities such as eating, drinking and exercise, cystine excretion is routinely measured using a composite urine sample collected over the course of a typical day. A urine sample collected over a 24-hour period is preferred for measuring cystine supersaturation in the assay of the present invention. It is understood, however, that a single voided urine sample or a sample from a urine collection taken over the course of less than or greater than 24 hours can also provide useful information.

A typical 24-hour urine collection can range in volume from about 500 ml to greater than 4000 ml. Since the diagnosis and monitoring of a cystinuria patient is routinely done on an outpatient basis, there are safety and logistical problems associated with the 24-hour urine collection process and subsequent transport of the urine collection to the laboratory. For example, the actual transport of a 500–4000 ml sample either by the patient, patient representative, or a delivery service to a clinical laboratory can be hazardous (e.g., breakage or spillage from the collection receptacle). A 24-hour urine collection from a cystinuria patient often has precipitated, crystallized cystine, making it impossible for either the patient or a patient representative to remove an aliquot of the urine collection for transport which accurately represents actual cystine concentration.

A urine collection process has now been found which enables a patient or a patient representative to collect a high volume urine specimen and subsequently transport a small volume sample to the laboratory. For example, with the collection process of the present invention, a patient can collect urine in a collection receptacle over a 24-hour period (e.g., 600–4000 ml), transfer a small volume aliquot of untreated urine to a first transport container, treat the remaining urine collection with a cystine-dissolving agent according to the collection process of the present invention, and then transfer a small volume aliquot of the treated urine to a second transport container, with the aliquot of untreated urine in the first transport container being useful in a cystine supersaturation assay and the aliquot of treated urine in the second transport container accurately representing the cystine concentration of the entire 24-hour collection.

During the collection process, voided urine is collected in a collection receptacle capable of holding the entire volume of voided urine. Since the solubility of cystine decreases as temperature decreases, the urine collected for the present invention is preferably not refrigerated and is retained at approximately room temperature throughout the collection period. The assay of the present invention can be performed using a urine collection that has been refrigerated; however, the amount of cystine crystallization may increase, thus requiring additional caution in preparing the samples for transport as discussed below. Because microbial growth has been reported to alter the chemistry, pH or microbiological contents of a urine sample over time, use of preservatives can be used in urine samples subject to collection and transport. While any antimicrobial system known in the art of urine preservation can be used, a preferred system is a combination of gentamicin (preferably about 40 mg per 3.5 liter urine container) and thymol (preferably about 100 mg per 3.5 liter urine container).

To perform the cystine supersaturation assay of the present invention, the solubility of cystine in the patient's original untreated urine is measured. There can also be an advantage of measuring cystine concentration of both treated and untreated urine samples as discussed below. Moreover, routine chemical urinalysis is often performed using aliquots of the collected urine; however, alkalinization or acidification of the urine can interfere with some of these tests. Consequently, the urine collection process of the present invention includes a step wherein the contents of the collection receptacle are mixed at the end of the collection process and an untreated aliquot (e.g., 50–100 ml) is transferred into a separate container for subsequent transport to the laboratory for analysis.

To the remaining collected urine, a cystine-dissolving agent is added in an effective amount which raises the pH of the urine to above pH 9, or a cystine-dissolving agent is added in an effective amount which lowers the pH of the urine below pH 2, to form a treated urine collection. In one embodiment, a fixed amount of cystine-dissolving agent capable of adjusting the pH of a specific volume of urine is provided to the patient or patient representative for dispensing in the collected urine. For example, a fixed amount of cystine-dissolving agent for treating a 24-hour urine collection can be provided with a 24-hour urine collection receptacle; or a fixed amount of cystine-dissolving agent for treating a single voided urine sample can be provided with a routine urine cup. Alternatively, an unmeasured amount of cystine-dissolving agent is provided along with a pH monitoring product such as a colorcoded, pH-sensitive dipstick typically used in the art which can be used to determine when a sufficient amount of the cystine-dissolving agent has been added to the urine collection. A preferred cystine-dissolving agent is sodium carbonate useful in a 24-hour urine collection at an effective amount of 15 grams.

The treated urine collection is mixed to dissolve any cystine which may have precipitated during the collection process. In one embodiment, following the removal of the untreated aliquot as discussed above, an effective amount of the cystine-dissolving agent is added to the collection receptacle at the end of the collection process, the treated urine collection is repeatedly mixed over time to redissolve any crystallized cystine, and an aliquot of the treated urine collection is then transferred into a separate container for subsequent transport to the laboratory for analysis. For example, the treated urine collection is thoroughly mixed immediately upon addition of the cystine-dissolving agent, mixed again after 30 minutes and again after 60 minutes, and an aliquot (e.g., 50–100 ml) of the treated urine collection is then transferred into a transport container. If the urine collection is refrigerated during the collection process, the treated urine collection may need to be mixed for more than 60 minutes prior to removing the treated aliquot.

The present invention includes a urine collection kit specific for obtaining urine samples suitable for the measurement of cystine concentration and cystine supersaturation. In one embodiment, the kit contains (1) a urine collection receptacle of suitable size to collect a predetermined amount of urine, in particular, from a single voided specimen to a 24-hour collection; (2) an aliquot of cystine-dissolving agent suitable for alkalinizing or acidifying the volume of collected urine to be added to the urine collection; (3) instructions describing the method of collecting urine and dispensing of cystine-dissolving agent into collected urine; and optionally, (4) transport containers for sending the treated sample and untreated aliquots to the laboratory for analysis. In another embodiment, the kit contains (1) a urine collection receptacle of suitable size to collect a predetermined amount of urine, in particular, from a single voided specimen to a 24-hour collection, wherein the receptacle contains a quantity of cystine-dissolving agent suitable for alkalinizing or acidifying the volume of urine to be collected; (2) instruction document for the patient regarding the method of collecting urine; and optionally, (3) transport containers for sending the treated and untreated aliquots to the laboratory for analysis.

An assay has also been found which provides for direct measurement of supersaturation even for patients undergoing treatment with therapeutic cystine-binding drugs. The assay can be performed using the untreated and treated aliquots of the urine collection prepared by the patient or patient representative according to the urine collection method of the present invention described above. Alternatively, the entire urine collection can be transported to the laboratory, and laboratory personnel can remove the untreated aliquot and add a cystine-dissolving agent to form the treated urine collection. In analyzing cystine concentration in the urine, it is preferable that cystine concentration is measured in both untreated and treated aliquots of the urine collection. If the treated aliquot has a higher concentration of cystine than the untreated aliquot, this indicates there must have been crystallization during the collection. In this situation, the cystine concentration of the treated aliquot is used to calculate cystine excretion. The untreated aliquot is used to measure cystine solubility and cystine supersaturation as given below, and optionally, other routine urinalysis procedures.

To the untreated aliquot of the urine collection is added solid phase cystine at a level well above the solubility of cystine in urine. Generally, in average normal urine, the solubility of cystine is 200 to 400 mg/liter. However, it can be appreciated that variations in compositions of normal and patient urines may affect solubility, and the amount of added solid phase cystine necessary to exceed the solubility in urine may vary accordingly. In the assay of the present invention, an effective amount of solid phase cystine is defined as an amount which results in a measurable amount of residual solid phase cystine remaining in the urine sample after incubation at about human body temperature (ca 37° C.) with stirring or mixing for at least about 48 hours as described below. The upper limit of added solid phase cystine is not critical; therefore, solid phase cystine can be added in any amount which results in a measurable amount of residual solid phase cystine after incubation. The lower limit of added solid phase cystine is important in that if an insufficient amount is added, the entire amount of solid phase cystine will dissolve in the urine sample, leaving no measurable residual solid phase cystine, indicating cystine saturation was not achieved. An effective lower limit of added solid phase cystine which will result in measurable residual solid phase cystine in the majority of urine samples generally ranges from about 400 to 800 mg/L of urine. It is to be understood that some urine samples may require less than 400 mg/L, while others may require more than 800 mg/L solid phase cystine. Should cystine saturation not be achieved at a added solid phase cystine within this range, the assay of the present invention can be repeated using a higher amount of added solid phase cystine.

Alternatively, the cystine solubility limit for a given urine sample can be estimated by performing a solubility screening test. In an exemplary solubility screening test, aliquots of the untreated urine collection are added to a series of tubes with increasing measured amounts of solid phase cystine added to each tube (e.g., 400, 600, 800, 1000, 1200 mg solid phase cystine/L of urine); the tubes are incubated at about 37° C. and then tested for the presence of residual solid phase cystine at 48 hours; after incubation, the tubes are examined for residual solid phase cystine by methods including but not limited to visual inspection for turbidity or using spectrophotometry; any concentration showing residual solid phase cystine at the end of the screening test incubation period can be used in the assay. As used hereinafter, an amount of added solid phase cystine which will result in residual solid phase cystine after the incubation period is referred to as an "effective amount of solid phase cystine."

In the cystine supersaturation assay, an effective amount of solid phase cystine is added to the untreated aliquot of the urine collection as described above to form a solid phase cystine/urine sample. Knowing the amount of cystine added and the volume of the aliquot of urine used, the maximal concentration of cystine in the urine from the added solid phase cystine (in moles per liter) can be calculated and is noted as $M_t$. The solid phase cystine/urine sample is then incubated until the solid phase cystine reaches equilibrium with the cystine dissolved in the urine. This is preferably accomplished by incubating the urine at about human body temperature (ca 37° C.) with stirring or mixing for at least about 48 hours.

After incubation, residual solid phase cystine is then separated from the solid phase cystine/urine sample to form a cystine pellet by any means known in the art, e.g., centrifugation or filtration. The cystine pellet is dissolved in an aliquot of cystine-dissolving agent of sufficient volume to completely dissolve the cystine pellet, preferably having the same volume as that of untreated aliquot used at the start of the assay (e.g., 25 ml) to form a final cystine solution.

Cystine concentration is then determined in both the urine sample from which the residual solid phase cystine has been removed ($M_d$) and the final cystine solution ($M_p$) by any means known in the art, e.g., colorimetric assays, HPLC, gas chromatography, or amino acid analysis (Nakagawa, Y. and Coe, F. L. 1999. *Clin Chim Acta* 28:57–68; Kaniowska, et al. 1998. *J Chromatog* 798:27–35; Pastore, et al. 1998. *Clin Chem* 44:825–832; Kurara, et al. 1999. *J Chromatog B* 731:141–147). The concentration (moles per liter) of solid phase cystine which dissolved into the patient urine sample ($M_d$) is calculated by subtracting the concentration (moles per liter) of cystine dissolved in the final cystine solution ($M_p$) from the concentration (moles per liter) of solid phase cystine initially added to the patient urine sample ($M_t$), i.e., $$M_d = M_t - M_p$$

In the absence of thiol drugs in the urine, calculated $M_d$ should match the measured $M_d$ for non-cystinuria patients. For cystinuria patients, calculated $M_d$ plus the amount of cystine in the patient's urine should match the measured $M_d$ in the absence of thiol drugs in the urine. However when thiol drugs are present in the urine, the measured cystine concentration in the urine may not be accurate, and the measurement of solid phase cystine remaining after incubation becomes a valid marker of supersaturation. By assaying urine samples taken from a patient on different occasions, changes in the concentration of residual solid phase cystine in the final cystine solution ($M_p$) as well as the ratio of $M_d$ to $M_p$ over time can be used to monitor changes in the patient's urine cystine supersaturation, wherein a decrease in $M_p$ indicates a decreased risk for cystine stone formation, and an increase in $M_p$, an increased risk for cystine stone formation.

Because the amount of solid phase cystine is measured before and after 48 hours of incubation with urine, and the measurement after incubation is based upon residual solid phase separated from the urine and dissolved in a cystine-dissolving agent, adverse effects of drug interactions are avoided. Moreover, in urine, the dissolution of solid phase is an extremely accurate index of solution cystine uptake.

The results obtained with the assay of the present invention have been shown to be equivalent or better than those reported using alternative approaches to the problem of direct quantitative cystine assays in the presence of thiol drugs. Preferably, a reduction reaction/colorimetric assay is used to determine the cystine concentrations in the assay. Once the solid phase cystine is dissolved in cystine-dissolving agent, a simple reduction reaction is extremely precise and reliable, as shown in Example 1 below by the recovery of solid phase cystine in the experiments done without added drugs.

Overall, the solid phase assay of the present invention is a technically straightforward and a very reliable way of assessing cystine movement into and out of urine, that avoids complexity of measurement and interference by drugs in the patient sample. With the assay, one can assess the effectiveness of patient drug therapy and the possible need for change in dosing regimen or prescription. Given that drug side effects are to some extent dose related and that cystinuria, when not controlled, leads to large stones that may damage kidneys, the assay of the present invention is of great potential value for clinical management.

The present invention can be better understood in light of the following examples. It is to be understood that the examples below are representative of the invention and are intended to be illustrative of the invention, but are not to be construed to limit the scope of the invention in any way. Modifications may be made in the structural features of the invention without departing from the scope of the invention. It will be readily apparent to those skilled in the art that alternative materials and methods may also be utilized without departing from the scope of the invention. In particular, the method for measuring cystine concentration presented in Example 3 is merely representative and any methods known in the art for cystine concentration measurement can be used in the present invention.

EXAMPLE 1

Solid Phase Dissolution Assay—No Drugs Present in Sample

To 25 ml aliquots of incubation buffer (0.01 M phosphate, 0.0027 M potassium chloride, 0.137 M sodium chloride, pH 7.4, Sigma Aldrich Corp, Catalog # P-4417), increasing amounts of solid phase cystine (Sigma Aldrich Corp, St Louis, Mo., Catalog # C-6195) were added and incubated for 48 hours at 37° C. with stirring. Residual solid phase was then separated to form a supernatant and a pellet, and the pellet was dissolved in 25 ml of a cystine-dissolving agent, an alkalinizing buffer of 0.1 M sodium carbonate, pH 9.9, (Sigma Aldrich Corp, Catalog # S-7795), to form a final cystine solution. Cystine concentration was determined in both the supernatant and the final cystine solution according to the procedure given in Example 3. Various separation techniques were used for removing the pellet: (1) in one experiment, centrifugation was performed at 4000 rpm at 37° C. for 20 minutes; (2) in two experiments, separation was performed by filtration using a Metricel filter (Gelman Sciences, Ann Arbor, Mich.); and (3) in four experiments, centrifugation was performed at room temperature at 3800 rpm for 20 minutes. As all methods were equivalent in outcome, the latter was employed in all subsequent experiments.

The same protocol was repeated using urine from six normal women and four normal men. The urine samples were fresh voidings, collected with gentamicin as preservative, and incubated exactly as was the buffer.

Figure 1A:
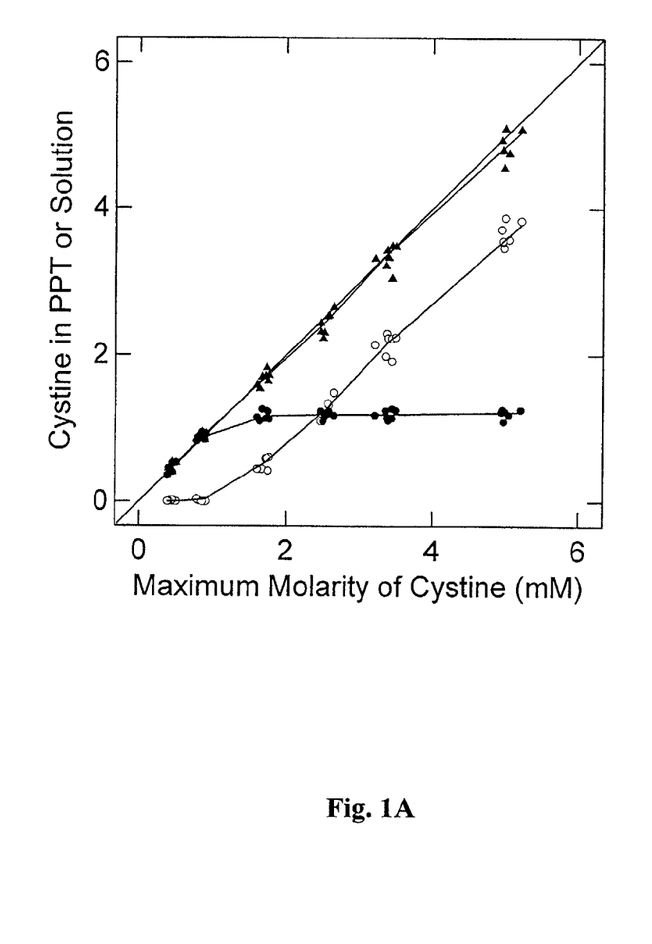
FIGS. 1A and 1B depict solid phase uptake of cystine into incubation buffer (FIG. 1A) or normal urine (FIG. 1B). Solution cystine concentration (filled circles) rises with increasing addition of solid phase cystine (x axis), until a stable solubility plateau is reached. Residual solid phase cystine (open circles) rises progressively, once buffer or urine becomes fully saturated; the sum of total cystine in the buffer or urine and residual solid phase at the conclusion of 48 hours of incubation (closed triangles) closely matches the total cystine added in the solid phase (points line up along the diagonal line of identity), showing complete analytical accounting for the total cystine between the liquid and solid phases. Each point represents a separate experiment in buffer and separate urine from a different individual. Six women and four men contributed urine samples.

Solid phase dissolution, or disappearance, accurately gauged solution uptake of cystine in simple buffer solution as shown in FIG. 1A. Solution cystine concentration (filled circles) rose to a stable plateau as more solid phase cystine was provided (x axis). Thereafter, surplus solid cystine (open circles) increased proportionally to the amount added. Importantly, the sum of measured solution ($M_d$) and residual cystine ($M_p$) exactly matched the total cystine available ($M_t$), i.e., $M_d+M_p=M_t$, so that measured total cystine (closed triangles) fell along the diagonal line of identity, matching the amount of cystine weighed into the assay tubes. The mean 4 plateau values, which reflect the solubility of cystine in this buffer, were 1.17, 1.18, 1.18, and 1.21 mM/L for the 4 clusters (filled circles). Thus, these data indicate that if the increase of solution concentration of cystine cannot be directly measured, the increase in solution concentration can be calculated very accurately from the disappearance of solid phase cystine in this system, given the amount of solid phase cystine added to the buffer.

Figure 1B:
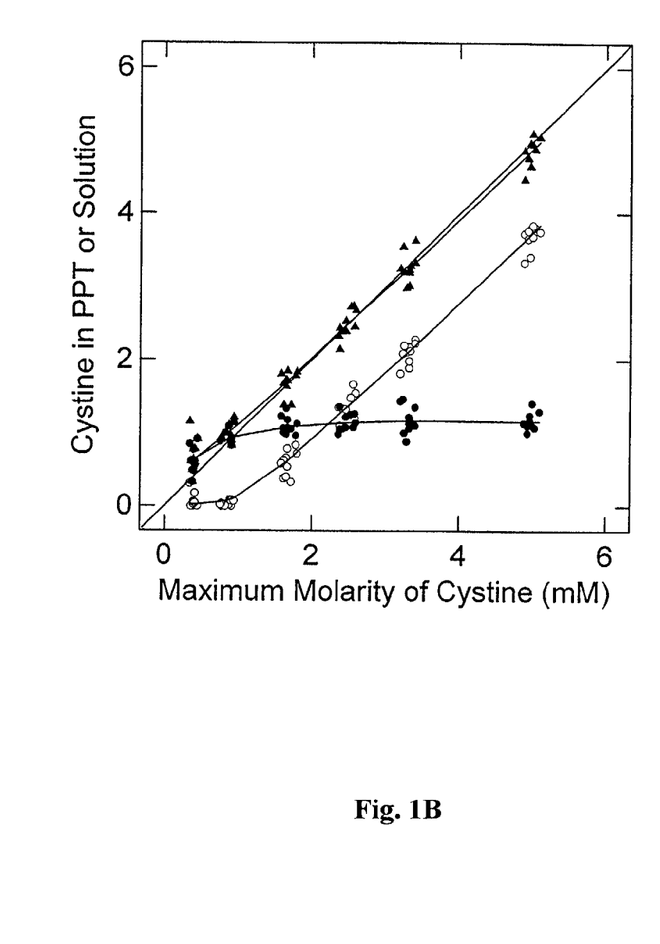
Figure 2A:
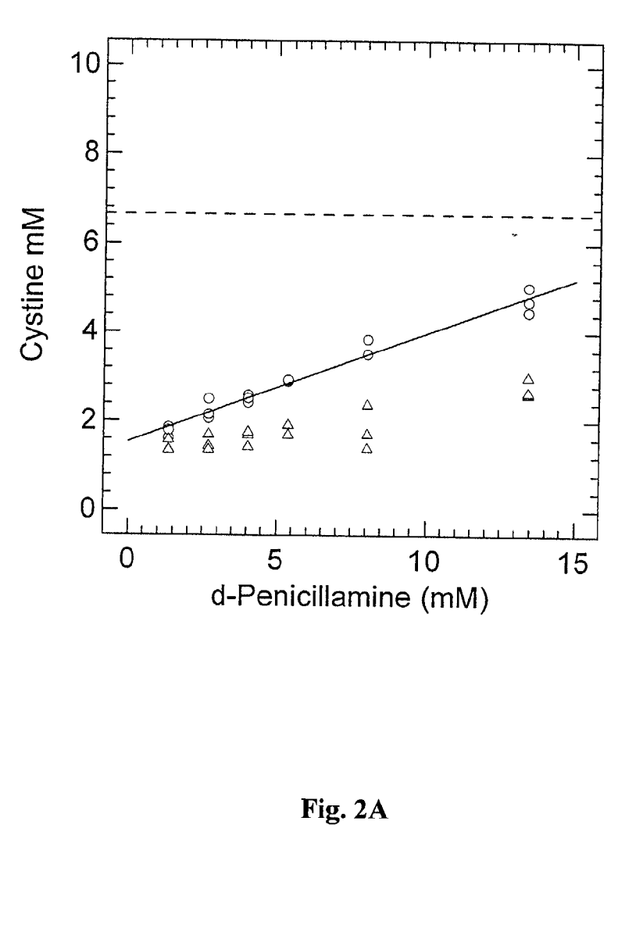
Figure 2B:
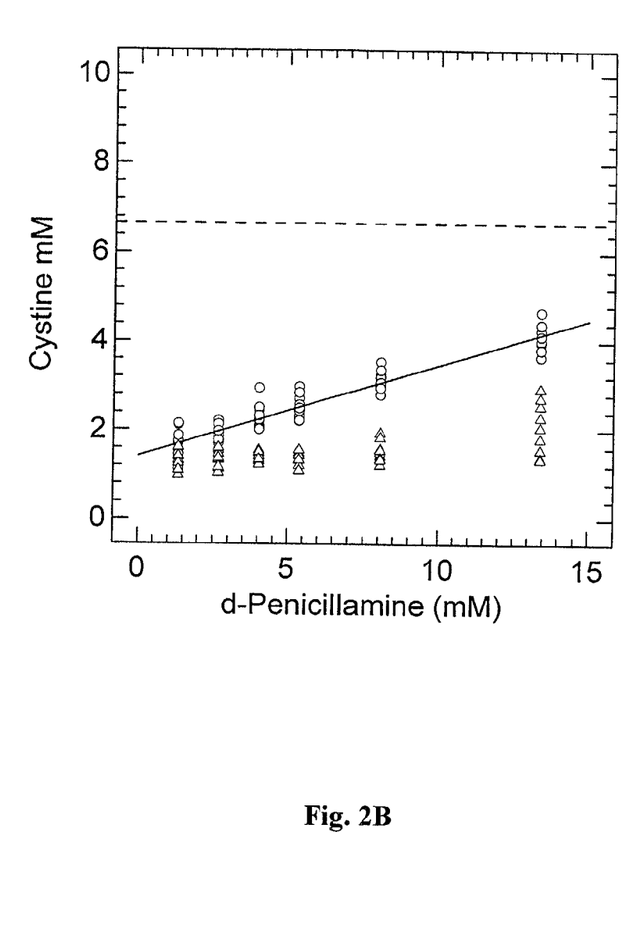
Figure 3A:
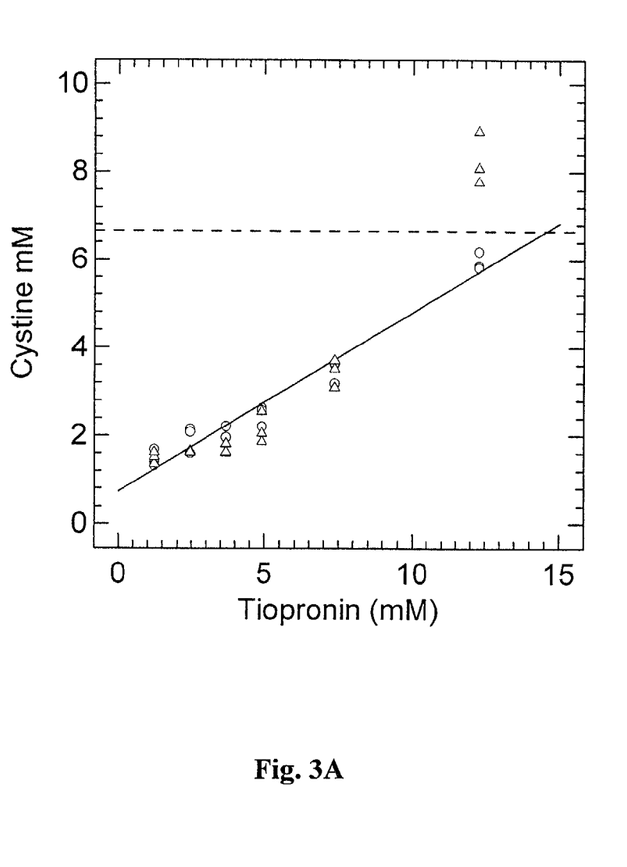
Figure 3B:
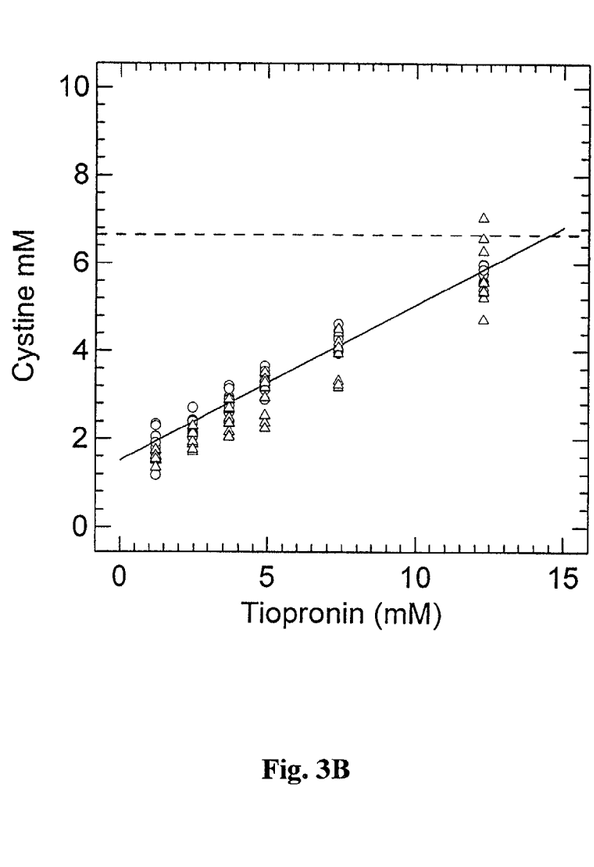
Figure 4A:
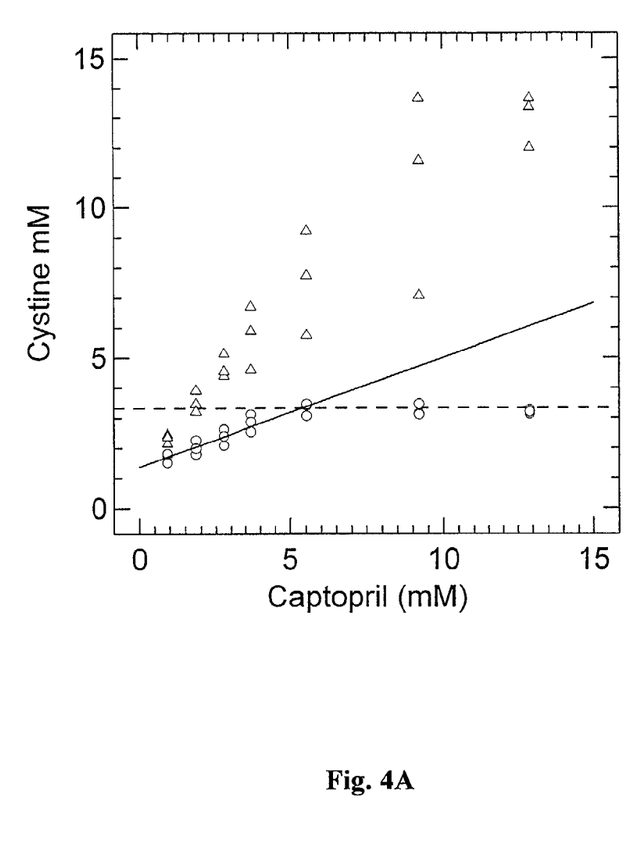
Figure 4B:
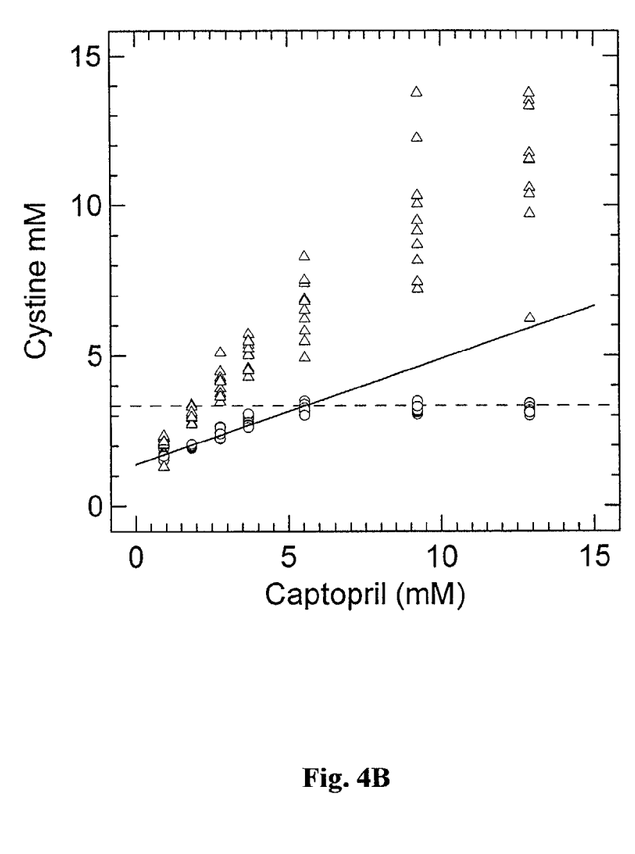

Solid phase dissolution also gauged the uptake of cystine into normal urine as shown in FIG. 1B. The mean 4 plateau values, which reflect the solubility of cystine in normal urine, were 1.09, 1.14, 1.18, and 1.16 mM/L (filled circles), i.e., the same as for the buffer. The ten urine samples, as expected, had a more variable cystine solubility than the buffer, so solution levels at the plateau spread (CV values for the 4 plateau points were 0.05, 0.04, 0.05 and 0.05 vs 0.12, 0.11, 0.16 and 0.10 for buffer and urine, respectively). Amounts of solid cystine left after the incubation spread correspondingly. However, as was the case for buffer, the total cystine calculated from urine (filled circles) and solid (open circles) measurements closely matched the amounts weighed in as can be seen by the calculated amounts (closed triangles) falling along the diagonal line of identity, meaning that the assay system successfully recovered the total cystine from the two phases, and that uptake into urine would therefore be as accurately measured from the disappearance of solid phase cystine in urine as in the buffer.

EXAMPLE 2

Effects of Cystine Binding Drugs on Solid Phase Dissolution Assay

Using the same incubation buffer and cystine-dissolving agent systems as for the initial solid phase dissolution assay given in Example 1, increasing amounts of D-penicillamine, tiopronin, or captopril were added to 25 ml aliquots of the incubation buffer. A fixed amount of cystine was added; for tiopronin and D-penicillamine, about 40 mg, and for captopril about 20 mg. The lower amount of solid phase cystine for captopril reflects the lower molarity attainable clinically with this drug in urine. Incubation was carried out as in Example 1. After 48 hours, the pellet and supernatant were separated by centrifugation, the pellet was dissolved in 25 ml of cystine-dissolving agent, an alkalinizing buffer of 0.1 M sodium carbonate, pH 9.9, (Sigma Aldrich Corp, Catalog # S-7795), to form a final cystine solution. Cystine concentration was determined both in the supernatant and the final cystine solution according to the procedure given in Example 3. This same protocol was repeated using the ten normal urine samples employed in the basic solid phase dissolution study described in Example 1. The results are summarized in Table I and FIGS. 2A, 2B, 3A, 3B, 4A and 4B.

Addition of D-penicillamine at increasing molarity caused progressive dissolution of solid phase cystine (y axis) into buffer (FIG. 2A) and urine (FIG. 2B), respectively. The slope of uptake on drug molarity was lower in urine than buffer (Table I), and the difference was significant (homogeneity of slopes p=0.02, significance of regression, p<0.0001). The intercepts were not different (Table I). Direct solution measurements in buffer or urine (triangles) were low and showed little slope dependence on drug molarity, meaning that without the solid phase assay, uptake could not have been measured accurately.

TABLE I

REGRESSION SLOPES AND INTERCEPT VALUES

| | BUFFER | | URINE | |
|---|---|---|---|---|
| | Slope | Intercept | Slope | Intercept |
| D-Penicill-amine | 0.25 ± 0.01 | 1.54 ± 0.07 | 0.21 ± 0.01* | 1.41 ± 0.06 |
| Tiopronin | 0.41 ± 0.02# | 0.73 ± 0.13 | 0.36 ± 0.01**# | 1.51 ± 0.06* |
| Captopril | 0.36 ± 0.04# | 1.38 ± 0.12 | 0.35 ± 0.01# | 1.36 ± 0.04 |

*differs from buffer, same drug, p < 0.02
**differs from buffer, same drug, p < 0.001
differs from D-Penicillamine, same solution, p < 0.001

Tiopronin added to buffer (FIG. 3A) or urine (FIG. 3B) dissolved cystine from the solid phase. In buffer, the uptake curve is not as linear as in urine. As shown in Table I, slopes and intercepts differ in urine and buffer, the latter because of an unusually low intercept value in buffer (Table I). Solution measurements (triangles) were not as different from dissolution values as shown with D-penicillamine, but at high drug levels in buffer or urine, points separated. Also, the scatter of points was greater in solution. As expected from the higher slope value in buffer and urine, tiopronin slopes differed from those of D-penicillamine (Table I), suggesting a higher molar binding capacity or affinity for tiopronin than D-penicillamine in both systems.

Captopril added to buffer (FIG. 4A) or urine (FIG. 4B) dissolved cystine in a linear progressive manner up to 6 mM/L. Sufficient solid phase cystine was not added to explore dissolution at higher drug molarities, as they cannot be reached clinically, but drug was added to those levels to explore solution chemistry (data not shown). Slopes for the 5 points up to and including the saturation line were not different in buffer vs urine (Table I), nor were the intercepts. Slopes in buffer and urine, respectively, did not differ from tiopronin but did from D-penicillamine (Table I). Solution reaction (triangles) rose progressively with drug addition, to levels far above the available solid phase cystine (dashed horizontal line), indicating probable reaction of the drug with the assay.

In summary, D-penicillamine had a lower molar dissolution slope compared to the other two drugs (Table I), whereas tiopronin and captopril were similar. For D-penicillamine and tiopronin, slopes were lower in urine than buffer. All intercepts were about the same except for tiopronin in buffer, which was very low (Table I), and the uptake curve was not quite linear for this drug in buffer, indicating a strong dependence of its action upon the milieu in which it is dissolved. Moreover, tiopronin was the one drug for which solution measurements tracked actual cystine uptake to a reasonable degree of accuracy.

Figure 5A:
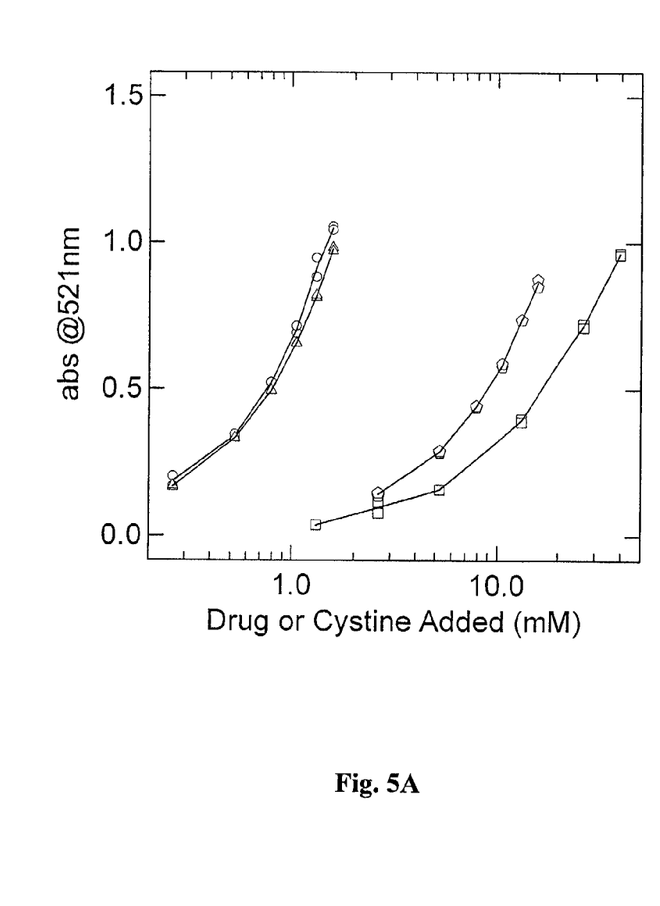
Figure 5B:
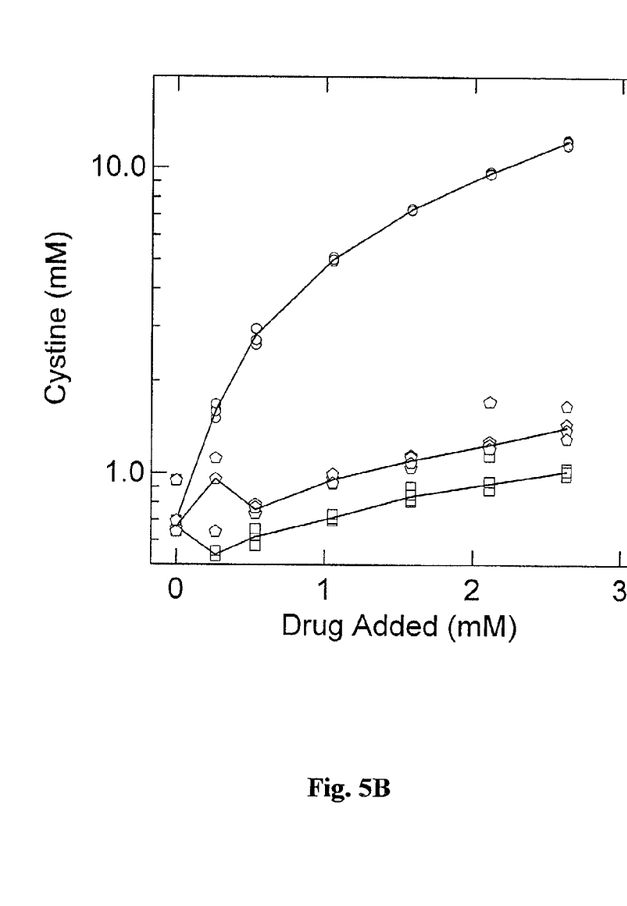

The contrasting behaviors of D-penicillamine, tiopronin, and captopril with respect to solution measurement can be explained by differences in their reaction with cystine and the assay system of the present invention. In the assay, captopril and cystine reacted alike, whereas D-penicillamine and tiopronin caused no reaction color until their concentration reached over 1 log (FIG. 5A). This explains the very high solution levels of color reaction with captopril seen in FIGS. 4A and 4B. When added to a saturated solution of cystine in buffer, D-penicillamine initially reduced the reaction signal, whereas tiopronin and captopril did not (FIG. 5B). D-penicillamine appeared to bind the cystine to form a complex that did not react with the system, whereas tiopronin and captopril complexes reacted. Thereafter, as drug concentration increased far above the solution cystine concentration, the assay measured free drug (FIG. 5B). Captopril caused a large signal increase, and tiopronin caused a lesser increase. These data explain the low solution values for D-penicillamine (presumably drug binding of cystine in an unmeasured complex) and the reasonable correspondence of measured and actual solution cystine uptake with tiopronin (modest drug reaction with the assay system and reaction of the assay to the drug-cysteine complex). As expected, addition of captopril progressively increased the assay signal, reflecting a reaction of the assay system with the free drug and drug bound cysteine with more or less of the sensitivity obtained with cystine alone (FIG. 5B).

EXAMPLE 3

Cystine Assay

Cystine concentrations in either the incubation buffer or normal urine after removal of the residual solid phase cystine, or the final cystine solution after the dissolution of the solid phase cystine in a cystine-dissolving agent as shown in Example 1 and 2 were measured using the modified cyanide-nitroprusside method for quantifying urinary cystine concentration as reported by Nakagawa and Coe (Nakagawa, Y. and Coe, F. 1999. *Clin Chim Acta* 289: 57–68). A 100 microliter aliquot was mixed with 400 microliters of water and 1 milliliter of 0.01 M sodium phosphate buffer containing 0.15 mol/liter NaCl, pH 7.3 (PBS). After adding 300 microliters of 10% NaCN aqueous solution (w/v), the sample was incubated for twenty minutes at room temperature. Color was developed by adding 100 microliters of 20% sodium nitroprusside aqueous solution (w/v). Within 20 seconds of the sodium nitroprusside addition, color intensity was then measured at 521 nm using a Beckman spectrophotometer (model DU 640), and cystine concentration was calculated by comparison to a standard curve which was prepared with each assay.

EXAMPLE 4

Solid Phase Dissolution Assay in Cystinuric Urine

A patient with cystinuria performs a 24-hour urine collection as part of the diagnostic evaluation. At the end of the collection process, an aliquot of untreated urine is withdrawn and submitted to the laboratory for routine chemistries, pH, and measurement of cystine concentration and cystine supersaturation. To prevent underestimation of the true urine cystine concentration caused by cystine crystallizing during the collection process, the rest of the 24-hour collection is treated with an alkalinizing cystine-dissolving agent such as sodium carbonate or an acidifying cystine-dissolving agent such as hydrochloric acid, and an aliquot is sent to the laboratory for measurement of cystine concentration. Using the untreated and treated aliquots, cystine supersaturation is then measured as described above, and the patient's cystine excretion rate is determined.

Should the patient demonstrate cystinuria, a physician may direct the patient to increase fluid intake, prescribe alkali salts to raise urine pH, and/or prescribe a drug such as tiopronin to bind cysteine in the urine. Periodically during treatment (e.g., once a month), the patient performs another 24-hour urine collection, and the assay for determining cystine supersaturation is repeated. If the prescribed treatment for cystinuria is effective, the assay results for subsequent 24-hour collections show the added solid phase cystine goes in solution, indicating an undersaturated urine with a much higher cystine solubility than that found on the initial urine collection. Any possible interference caused by the prescribed drug in measuring cystine supersaturation is negated by the solid phase assay.

Statistics

Routine means and t tests and linear regression analysis used standard statistical software (Systat, SPSS Corp., Chicago, Ill.). Differences in slopes of uptake with drugs were assessed by multivariate analysis in which cystine uptake was the dependent variable; drug molarity, the independent variable; either buffer vs urine or drug type, the categorical variable; and probability of homogeneity of slopes between the groups, defined by the categorical variable tested. Simple regression analysis was used to obtain the actual values of the slopes.

We claim:

1. A method for determining the level of cystine supersaturation in a patient urine sample comprising
   a. adding to said patient urine sample a measured amount of solid phase cystine to form a cystine/urine sample;
   b. incubating said cystine/urine sample under conditions that permit dissolution of said solid phase cystine until equilibrium is reached with undissolved residual solid phase cystine to form an equilibrium mixture;
   c. separating said residual solid phase cystine from said equilibrium mixture to form a cystine pellet;
   d. completely dissolving said cystine pellet in a cystine-dissolving agent to form a final cystine solution;
   e. measuring the amount of cystine dissolved in said final cystine solution; and
   f. subtracting the amount of cystine dissolved in said final cystine solution from said measured amount of solid phase cystine to obtain a calculated value for the amount of dissolved solid phase cystine in said equilibrium mixture, whereby said amount of dissolved solid phase cystine in said equilibrium mixture is an indicator of urine cystine supersaturation.

2. The method of claim 1, wherein said patient urine sample is an aliquot of voided urine collected over a 24-hour period.

3. The method of claim 1 or 2, wherein said final cystine solution has a pH greater than pH 9.

4. The method of claim 3, wherein said cystine-dissolving agent is selected from the group consisting of sodium carbonate, sodium bicarbonate, lithium carbonate, sodium hydroxide and potassium hydroxide.

5. The method of claim 1 or 2, wherein said final cystine solution has a pH less than pH 2.

6. The method of claim 5, wherein said cystine-dissolving agent is selected from the group consisting of hydrochloric acid, sulfuric acid, phosphoric acid, and nitric acid.

7. A method for measuring a patient's risk for cystine stone formation comprising
   a. adding to a first patient urine sample at a first time point a measured first amount of solid phase cystine to form a first cystine/urine sample;
   b. incubating said first cystine/urine sample under conditions that permit dissolution of said solid phase cystine until equilibrium is reached with undissolved residual solid phase cystine to form a first equilibrium mixture;
   c. separating said first residual solid phase cystine from said first equilibrium mixture to form a first cystine pellet;
   d. completely dissolving said first cystine pellet in a first cystine-dissolving agent to form a first final cystine solution;
   e. measuring the amount of cystine dissolved in said first final cystine solution;
   f. subtracting the amount of cystine dissolved in said first final cystine solution from said first measured amount of solid phase cystine to obtain a calculated value for the amount of dissolved solid phase cystine in said first equilibrium mixture;
   g. at a second time point adding to a second patient urine sample collected under the same conditions as said first patient urine sample a measured second amount of solid phase cystine to form a second cystine/urine sample;
   h. incubating said second cystine/urine sample under conditions that permit dissolution of said solid phase cystine until equilibrium is reached with undissolved residual solid phase cystine to form a second equilibrium mixture;
   i. separating said second residual solid phase cystine from said second equilibrium mixture to form a second cystine pellet;
   j. completely dissolving said second cystine pellet in a second cystine-dissolving agent, said first cystine-dissolving agent and said second cystine-dissolving agent being the same or different, to form a second final cystine solution;
   k. measuring the amount of cystine dissolved in said second final cystine solution;
   l. subtracting the amount of cystine dissolved in said second final cystine solution from said second measured amount of solid phase cystine to obtain a calculated value for the amount of dissolved solid phase cystine in said second equilibrium mixture; and
   m. comparing the amount of dissolved solid phase cystine in said first equilibrium mixture to the amount of dissolved solid phase cystine in said second equilibrium mixture;
   whereby an increase in the amount of dissolved solid phase cystine in said second equilibrium mixture over the amount of dissolved solid phase cystine in said first equilibrium mixture is equated with a lesser risk of cystine stone formation in said patient and a decrease in the amount of dissolved solid phase cystine in said second equilibrium mixture over the amount of dissolved solid phase cystine in said first equilibrium mixture is equated with a greater risk of cystine stone formation in said patient.

8. The method of claim 7, wherein said first patient urine sample is an aliquot of a urine collection voided over a 24-hour period at said first time point and wherein said second patient urine sample is an aliquot of a urine collection voided over a 24-hour period at said second time point.

9. The method of claim 7 or 8, wherein the pH of said first final cystine solution is greater than pH 9 or less than pH 2 and wherein the pH of said second final cystine solution is greater than pH 9 or less than pH 2.

10. The method of claim 9, wherein said first and said second cystine-dissolving agent is selected from the group consisting of sodium carbonate, sodium bicarbonate, lithium carbonate, sodium hydroxide potassium hydroxide, hydrochloric acid, sulfuric acid, phosphoric acid, and nitric acid.

11. A method for determining cystine concentration in a patient urine comprising
   a. collecting voided urine over time in a collection receptacle to form an untreated urine collection;
   b. transferring an aliquot of said untreated urine collection to a second container to form an untreated urine sample;
   c. adding to said untreated urine collection an effective amount of a cystine-dissolving agent to completely dissolve any crystallized cystine present in said urine collection to form a treated urine collection having a pH less than pH 2;
   d. measuring the cystine concentration in said treated urine collection and in said untreated urine sample;
   e. comparing the cystine concentration in said treated urine collection to the cystine concentration in said untreated urine sample, and
   concluding that the cystine concentration of said patient urine is the measured cystine concentration of the untreated urine sample if the measured cystine concentration of the treated urine collection is less than or equal to the measured cystine concentration of the untreated urine collection or concluding that the cystine concentration of said patient urine is the measured cystine concentration of the treated urine collection if the measured cystine concentration of the treated urine collection is higher than the measured cystine concentration of the untreated urine sample.

12. The method of claim 11, wherein said patient collects voided urine over a 24-hour period to form said untreated urine collection.

13. The method of claim 11 or 12, wherein said cystine-dissolving agent is selected from the group consisting of hydrochloric acid, sulfuric acid, phosphoric acid, and nitric acid.

14. A method for determining cystine concentration and the amount of cystine supersaturation in a patient urine sample comprising a. collecting voided urine over time in a collection receptacle to form an untreated urine collection;
b. transferring an aliquot of said untreated urine collection to a second container to form an untreated urine sample;
c. adding to said untreated urine collection an effective amount of a cystine-dissolving agent to completely dissolve any crystallized cystine present in said urine collection to form a treated urine collection;
d. determining the cystine concentration in said treated urine collection and said untreated urine sample;
e. comparing the cystine concentration in said treated urine collection to the cystine concentration in said untreated urine sample;
f. adding to an aliquot of said untreated urine sample a measured amount of solid phase cystine to form a cystine/urine sample;
g. incubating said cystine/urine sample under conditions that permit dissolution of said solid phase cystine until equilibrium is reached with undissolved residual solid phase cystine to form an equilibrium mixture;
h. separating said residual solid phase cystine from said equilibrium mixture to form a cystine pellet;
i. completely dissolving said cystine pellet in a cystine-dissolving agent to form a final cystine solution;
j. measuring the amount of cystine dissolved in said final cystine solution; and
k. subtracting the amount of cystine dissolved in said final cystine solution from said measured amount of solid phase cystine to obtain a calculated value for the amount of dissolved solid phase cystine in said equilibrium mixture, whereby said amount of dissolved solid phase cystine is an indicator of urine cystine supersaturation and concluding that the cystine concentration of said patient urine is the measured cystine concentration of the untreated urine sample if the measured cystine concentration of the treated urine collection is less than or equal to the measured cystine concentration of the untreated urine collection or concluding that the cystine concentration of said patient urine is the measured cystine concentration of the treated urine collection if the measured cystine concentration of the treated urine collection is higher than the measured cystine concentration of the untreated urine sample.

15. The method of claim 14, wherein said patient collects voided urine over a 24-hour period to form said untreated urine collection.

16. The method of claim 14 or 15, wherein the pH of said treated urine collection is greater than pH 9 or less than pH 2 and wherein the pH of said final cystine solution is greater than pH 9 or less than pH 2.

17. The method of claim 16, wherein said cystine-dissolving agent is selected from the group consisting of sodium carbonate, sodium bicarbonate, lithium carbonate, sodium hydroxide, potassium hydroxide, hydrochloric acid, sulfuric acid, phosphoric acid, and nitric acid.

* * * * *